United States Patent [19]

Mayer-Mader et al.

[11] 3,984,384

[45] *Oct. 5, 1976

[54] PROCESS USING DIALKOXY-XANTHOGENDISULPHIDES AS MOLECULAR WEIGHT REGULATORS

[75] Inventors: Rudolf Mayer-Mader, Cologne; Jürgen Boldt, Opladen, both of Germany

[73] Assignee: Bayer Aktiengesellschaft, Germany

[*] Notice: The portion of the term of this patent subsequent to Sept. 24, 1991, has been disclaimed.

[22] Filed: Aug. 7, 1974

[21] Appl. No.: 495,409

Related U.S. Application Data

[62] Division of Ser. No. 305,133, Nov. 9, 1972, Pat. No. 3,875,201.

[30] Foreign Application Priority Data

Nov. 13, 1971 Germany............................ 2156453

[52] U.S. Cl.......................... 526/223; 260/29.7 NQ; 260/890; 526/338; 526/340; 526/335
[51] Int. Cl.²................... C08F 4/00; C08F 220/42; C08F 136/16; C08C 136/02
[58] Field of Search.......... 260/82.7, 29.7 NQ, 83.5, 260/84.3, 92.3, 94.4, 890, 86.3, 86.7, 85.5 XA, 85.5 F, 87.5 R

[56] References Cited

UNITED STATES PATENTS

| | | | |
|---|---|---|---|
| 3,147,317 | 9/1964 | Jungk et al. | 260/890 |
| 3,147,318 | 9/1964 | Jungk | 260/890 |
| 3,300,433 | 1/1967 | Apotheker | 260/79 |
| 3,317,451 | 5/1967 | Apotheker | 260/79 |
| 3,580,830 | 5/1971 | Siebert | 260/79 |
| 3,635,864 | 1/1972 | McCarthy et al. | 260/79 |
| 3,838,140 | 9/1974 | Mayer-Mader et al. | 260/92.3 |
| 3,862,975 | 1/1975 | Csontos | 260/79 |

Primary Examiner—Joseph L. Schofer
Assistant Examiner—Herbert J. Lilling
Attorney, Agent, or Firm—Connolly and Hutz

[57] ABSTRACT

Dialkoxyxanthogendisulphides, their production by reacting an alcohol and carbondisulphide in the presence of alkali and subsequent oxydation, use of these dialkoxyxanthogendisulphides as molecular weight regulators in polymerization processes and a mixture of chloroprene-copolymers made in the presence of dialkoxyxanthogendisulphides.

5 Claims, No Drawings

PROCESS USING DIALKOXY-XANTHOGENDISULPHIDES AS MOLECULAR WEIGHT REGULATORS

CROSS-REFERENCE TO RELATED APPLICATION

This application is a division of application Ser. No. 305,133 filed Nov. 9, 1972, and now U.S. Pat. No. 3,875,201, granted on April 1, 1975.

This invention relates to dialkoxyxanthogendisulphides, to a process for their production and to a process for polymerising dienes in the presence of these dialkoxyxanthogendisulphides.

The dialkoxyxanthogendisulfides according to the invention correspond to the general formula (I):

$$R-O-\underset{\underset{S}{\|}}{C}-S-S-\underset{\underset{S}{\|}}{C}-O-R \quad (I)$$

wherein the R's are equal or different and each represents $R_1O(-CH_2-)_nO(-CH_2-)_{n'}-$ ;

$R_1O-R_2-$ ;

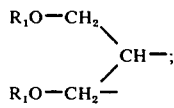

$R_3O(-CH_2)_m-$ $R_1$ being alkyl having 1 to 10 carbon atoms;
$R_2$ being linear or branched alkylene having 3 to 10 carbon atoms;
$R_3$ being alkyl having 3 to 10 carbon atoms;
$n$ and $n'$ = 2, 3 or 4; and
$m$ = 1 or 2.

Preferably both R's are equal. The following dialkoxyxanthogendisulfides are preferred:
di(3,6-dioxaheptyl-1)-xanthogendisulphide,
di(3,6-dioxaoctyl-1)-xanthogendisulphide,
di(3,6-dioxanonyl-1)-xanthogendisulphide,
di(3,6-dioxa-7-methyloctyl-1)-xanthogendisulphide,
di(3,6-dioxadecyl-1)-xanthogendisulphide,
di(3-oxa-5-isobutoxypentyl-1)-xanthogendisulphide,
di(3,6-dioxaundecyl-1)-xanthogendisulphide,
di(3-oxa-5-isopentoxypentyl-1)-xanthogendisulphide,
di(3,6-dioxadodecyl-1)-xanthogendisulphide,
di(3-oxa-5-isohexoxypentyl-1)-xanthogendisulphide,
di(3-oxa-hexyl-1)-xanthogendisulphide,
di(3-oxa-4-methylpentyl-1)-xanthogendisulphide,
di(3-oxa-heptyl-1)-xanthogendisulphide,
di(2-isobutoxyethyl-1)-xanthogendisulphide,
di(3-oxaoctyl-1)-xanthogendisulphide,
di(2-isopentoxypentyl-1)-xanthogendisulphide,
di(3-oxanonyl-1)-xanthogendisulphide,
di(2-isohexoxyethyl-1)-xanthogendisulphide,
di(2-methyl-3-oxabutyl-1)-xanthogendisulphide,
di(1-methyl-3-oxabutyl-1)-xanthogendisulphide,
di(2-methyl-3-oxapentyl-1)-xanthogendisulphide,
di(1-methyl-3-oxapentyl-1)-xanthogendisulphide,
di(5-oxahexyl-1)-xanthogendisulphide,
di(methoxyisobutyl)-xanthogendisulphide,
di(5-oxaheptyl-1)-xanthogendisulphide,
di(3-methyl-4-oxapentyl-1)-xanthogendisulphide,
di(1-ethoxmethyl-3-oxapentyl-1)-xanthogendisulphide, The invention also relates to a process for producing dialkoxyxanthogendisulphides of formula (I) wherein an alcohol ROH (R as defined above) is reacted with carbon disulphide in the presence of an alkali metal hydroxide to form the corresponding alkali xanthogenate which is then oxidised to form the corresponding xanthogendisulphide. Examples of suitable alcohols ROH are:

1. diethylene glycol monomethyl ether
2. diethylene glycol monoethyl ether
3. diethylene glycol monopropyl ether
4. diethylene glcyol monoisopropyl ether
5. diethylene glcyol monobutyl ether
6. diethylene glycol monoisobutyl ether
7. diethylene glycol monopentyl ether
8. diethylene glycol monoisopentyl ether
9. diethylene glycol monohexyl ether
10. diethylene glycol monoisohexyl ether
11. ethylene glycol monopropyl ether
12. ethylene glycol monisopropyl ether
13. ethylene glycol monobutyl ether
14. ethylene glycol monoisobutyl ether
15. ethylene glycol monopentyl ether
16. ethylene glycol monoisopentyl ether
17. ethylene glycol monohexyl ether
18. ethylene glycol monoisohexyl ether
19. propylene glycol monomethyl ether
20. isopropylene glycol monomethyl ether
21. propylene glycol monoethyl ether
22. isopropylene glycol monoethyl ether
23. butylene glycol monomethyl ether
24. isobutylene glycol monomethyl ether
25. butylene glycol monoethyl ether
26. 3-methoxy-1-butanol
27. 1,3-glycerin diethyl ether.

The process is generally carried out as follows: An alcohol ROH (R as defined above) and an aqueous alkali metal hydroxide solution are mixed at about 0° to 30° C so that the amounts of alcohol and of hydroxide are equimolar or approximately equimolar. The aqueous alkali metal hydroxide solution is preferably 20 to 50 % by weight. The preferred alkali hydroxides are sodium and potassium hydroxides.

Carbon disulphide is slowly added to this mixture in an amount from 1 to 10 times the equimolar amount of the alcohol. An exothermic reaction sets in at once and the reaction temperature is kept within the limits of 0° to 50° C by external cooling. In this reaction the alkali xanthogenate of the alcohol is formed as illustrated in the following equation:

$$\text{ROH} + \text{MeOH} + \text{CS}_2 \longrightarrow R-O-\underset{\underset{S}{\|}}{C}-S-Me + H_2O$$

Me = alkali metal; R as defined above.

To the resulting aqueous alkali xanthogenate solution there is then added a suitable oxidising agent in an amount of from 0.5 to 0.7 mols per mol of alkalixanthogenate, such as hydrogen peroxide or potassium peroxy disulphate (in the form of an aqueous solution) at a temperature of 10° to 40° C, preferably 20° C, causing formation of the corresponding xanthogendisulphide.

This product is water-insoluble and precipitates. It is separated from the aqueous phase (for example by filtration) and dried. The reaction taking place is illustrated in the following equation:

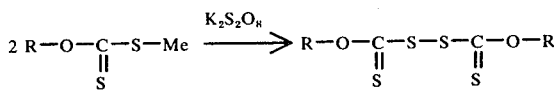

R as defined above.

This process is analogous to the known process for producing dialkylxanthogendisulphides described for example in Kirk-Othmer, Encyclopedia of Chemical Technology, 2nd Edition, Vol. 22 (1970), pages 419 – 429, and in Ullmann, Encyclopedie der Technischen Chemie, Vol. 18 (1967) pages 718 – 728.

The invention also relates to a process for polymerising conjugated diolefins and for copolymerising conjugated diolefins with α-olefins in the presence of radical initiators and of dialkoxyxanthogendisulphides of formula (I) as molecular weight regulators. Suitable conjugated diolefins include those having 4 to 8 carbon atoms, such as butadiene, isoprene and piperylene. Chloroprene and 2,3-dichlorobutadiene are preferred. Acrylonitrile, styrene and ethyl acrylate are preferred α-olefins. α-olefins can be copolymerised in quantities of up to 40 % by weight, based on the diolefin. Examples of suitable radical polymerisation catalysts include peroxides, azo compounds and so-called redox systems, i.e. combinations of peroxides and reducing compounds, such as: cumene hydroperoxide, pinane hydroperoxide, potassium peroxy disulphate, tert.-butyl hydroperoxide, azo-bis-isobutyronitrile; as well as cumene hydroperoxide, combined with formaldehyde sulphoxylate, iron salts or formamidine sulphinic acid.

Polymerisation is preferably carried out in aqueous emulsion, starting with an aqueous phase containing an emulsifier preferably in a quantity of from 0.1 to 5 % by weight. Examples of suitable emulsifiers include alkali alkyl sulphonates, alkali alkyl sulphates, long-chain carboxylic acids, resinic acids and polyether alcohols. The monomer or monomers is/are emulsified into the aqueous phase together with from 0.05 to 30 % by weight, preferably from 0.15 to 1 % by weight, based on monomer, of a dialkoxyxanthogendisulphide of formula (I). Subsequently the radical initiator is added. Polymerisation temperatures of −50° to +100° C and preferably 5° to 50° C are suitable (emulsion polymerisation of chloroprene is basically known see e.g. U.S. Pat. Nos. 3,042,652, 3,147,317 and 3,147,318).

At a conversion of 50 to 100 %, preferably 50 to 70 %, polymerisation is terminated, any unreacted monomer is removed, the polymer formed precipitated from the aqueous emulsion with an electrolyte or by low-temperature coagulation and then dried in the usual way. The dialkoxyxanthogendisulphides function as molecular weight regulators; they reduce the molecular weight of the polymers obtained compared with polymers made in their absence. This is demonstrated by comparing Mooney viscosities.

The dialkoxyxanthogendisulphides of the invention are especially molecular weight regulators in the polymerisation of chloroprene. Polychloroprene obtained in their presence has particularly favourable processing properties. These are most pronounced in mixtures of uncrosslinked benzene-soluble polychloroprenes produced in accordance with the invention and crosslinked benzene-insoluble polychloroprenes. In addition to favourable processing properties, these mixtures also have particularly high strength.

Accordingly, the invention also relates to a mixture of an uncrosslinked benzene-soluble chloroprene polymer (a) and a crosslinked benzene-insoluble chloroprene polymer (b), wherein the uncrosslinked benzene-soluble chloroprene polymer is a polymer of chloroprene and optionally up to 40 % by weight (based on monomer mixture) of an α-olefin prepared in the presence of from 0.05 to 30 % by weight (based on monomer) of a dialkoxyxanthogendisulphide of formula (I).

Accordingly, the benzene-soluble chloroprene polymer in this mixture is a product the preparation of which has been described above.

Crosslinked benzene-insoluble chloroprene polymers suitable for admixture with benzene-soluble chloroprene polymers can be obtained in latex form by various methods. For example, conventional chloroprene polymerisation can be continued to high (e.g. 90 to 100 %) conversion with no or only a small quantity of a chain-transfer agent, such as an alkyl mercaptan or a dialkylxanthogendisulphide. Such a process is described for example in U.S. Pat. No. 3,147,317. Alternatively chloroprene is copolymerized with a copolymerisable monomer containing two or more polymerisable double bonds. Examples of suitable comonomers include divinyl benzene and esters of methacrylic acid with polyhydroxy compounds, for example alkylene glycols, dihydroxy benzene or trimethylol propane, containing at least two methacrylic acid moieties.

In general, crosslinked chloroprene polymers are made by the same basic process which yields benzene-soluble chloroprene polymers, the only difference being that monomer conversion is increased, for example to from 90 to 100 %.

In another method of producing suitable crosslinked chloroprene polymers a latex of a benzene-soluble chloroprene polymer is subjected to a crosslinking post-treatment. Examples of suitable post-treatments are irradiation with actinic light as described in U.S. Pat. No. 3,042,652 and treatment with an organic peroxy compound as described in U.S. Pat. No. 3,147,318.

In the crosslinked chloroprene polymers up to about 20 % of the chloroprene can be replaced by another conjugated diolefins or α-olefins, examples of which are given in the description relating to the preparation of the benzene-soluble chloroprene polymers.

A copolymer of chloroprene and from 2 to 20 % by weight, based on chloroprene, of a diester of a dihydric aliphatic alcohol and an acrylic acid, is a preferred benzene-insoluble chloroprene polymer. These diesters correspond to the general formula (II):

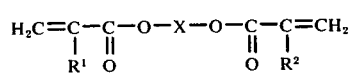

in which $R^1$ and $R^2$ represent hydrogen, an alkyl radical with from 1 to 4 carbon atoms of chlorine; and X represents an alkylene radical with from 2 to 20 carbon atoms.

Examples of such compounds include ethylene dimethacrylate, propylene dimethacrylate, butylene dimethacrylate, isobutylene dimethacrylate, ethylene diacrylate, propylene diacrylate, butylene diacrylate and isobutylene diacrylate.

Such copolymers are made by the conventional aqueous emulsion polymerisation used for making polychloroprene. These copolymers and the process for their manufacture are described in British Patent No. 1,158,970.

Mixtures of crosslinked and non-crosslinked chloroprene polymers are made, e.g. by thoroughly mixing them in latex form and subsequently recovering the solid polymer mixture, for example by low-temperature coagulation (as described in U.S. Pat. No. 2,187,146) or by drying on cylinders (as described in U.S. Pat. No. 2,914,497). It is also possible to mix the solid polymers mechanically, for example by kneading on mixing rolls or in an internal mixer (such as a Banbury mixer or a Werner-Pfleiderer mixer).

The weight ratio of the benzene-soluble dialkoxyxanthogendisulphide modified chloroprene polymer (a) to the crosslinked chloroprene polymer (b) is preferably from about 20 : 1 to 1 : 1, most preferably from 4 : 1 to 1 : 1.

The polychloroprene mixtures of the invention can be processed to form rubber mixtures and vulcanised in the same way as conventional polychloroprenes. They can be used for all purposes of conventional polychloroprenes. Their particular advantage is improved processing compared to benzene-soluble and benzene-insoluble polychloroprenes and improved stability under thermal stress compared with mixtures of conventional benzene-soluble and benzene-insoluble polychloroprenes.

Preparation of alkoxyxanthogendisulphides:

EXAMPLE 1

The xanthogendisulphide of diethylene glycol monoethyl ether 88 g of sodium hydroxide are dissolved in 90 g of pure water in a 3-liter-flask with stirring. 268 g of diethylene glycol monoethyl ether are then added and the mixture stirred for 2 hours. After cooling to 10°C 176 g of carbon disulphide are added dropwise with stirring, so that the temperature does not exceed 20° C; stirring is continued for a further 2 hours.

A solution of 300 g of ammonium persulphate in 2 liters of pure water is then run into the obtained reaction mixture of the xanthogenate formed. The xanthogendisulphide formed by oxidation precipitates, is filtered off, washed with pure water and redissolved in ethylether. The ether solution is dried with anhydrous sodium sulphate and the ether evaporated on a rotary evaporator. The yield of xanthogendisulphide is 297 g.

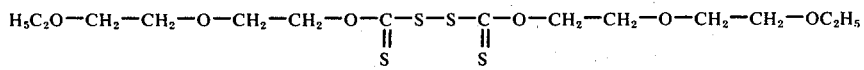

EXAMPLE 2

The xanthogendisulphide of 1,3-glycerin diethyl ether 150 g of sodium hydroxide are dissolved in 150 g of pure water in a 3-liter flask with stirring. 296 g of glycerin-1,3-diethyl ether are then added and the mixture stirred for 2 hours. After cooling to 10° C 152 g of carbon disulphide are added dropwise with stirring, so that the temperature does not exceed 20° C; stirring is continued for a further 2 hours.

A solution of 300 g of ammonium persulphate in 2 liters of pure water is then run into the obtained reaction mixture of the xanthogenate formed. The xanthogendisulphide formed by oxidation precipitates, is filtered off, washed with pure water, and redissolved in ether. The ether solution is dried with anhydrous sodium sulphate and the ether evaporated on a rotary evaporator. The yield of xanthogendisulphide is 221 g.

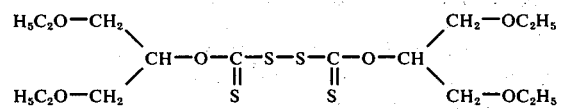

EXAMPLE 3

The xanthogendisulphide of 3-methoxy-1-butanol 88 g of sodium hydroxide are dissolved in 90 g of pure water in a 3-liter flask with stirring. 208 g of 3-methoxy-1-butanol are then added, and the mixture stirred for a further 2 hours. After cooling to 10° C, 176 g of carbon disulphide are added dropwise with stirring, so that the temperature does not exceed 20° C; stirring is continued for a further 2 hours. A solution of 300 g of ammonium persulphate in 2 liters of pure water is then run into the obtained reaction mixture of the xanthogenate formed. The xanthogendisulphide formed by oxidation precipitates, is filtered off, washed with pure water and redissolved. The ether solution is dried with anhydrous sodium sulphate and the ether evaporated on a rotary evaporator. The yield of xanthogendisulphide is 310 g.

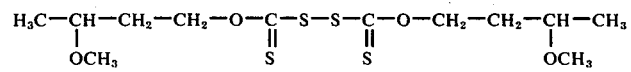

EXAMPLE 4

The xanthogendisulphide of propoxy ethylene glycol 88 g of sodium hydroxide are dissolved in 90 g of pure water in a 3-liter flask with stirring. 208 g of propoxy ethylene glycol are then added and stirring continued for 2 hours.

After cooling to 10° C 176 g of carbon disulphide are added dropwise with stirring so that the temperature does not exceed 20° C; stirring is continued for a further 2 hours. A solution of 300 g of ammonium persulphate in 2 liters of pure water is then run into the obtained reaction mixture of the xanthogenate formed. The xanthogendisulphide formed by oxidation precipitates, is filtered off, washed with pure water and redissolved in ether. The ether solution id dried with anhydrous sodium sulphate and the ether evaporated in a rotary evaporator. The yield is 323 g.

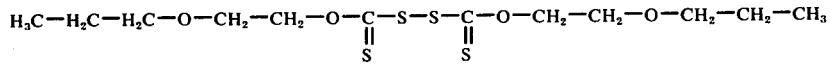

Alkoxyxanthogendisulphides as molecular weight regulators:

I. Polymerisation example

The following phases are separately prepared and introduced into the reaction vessel:

Monomer phase
100 parts by weight of chloroprene and
$y$ parts by weight of the xanthogendisulphide of 3-methoxy-1-butanol Aqueous phase
120 parts by weight of pure water,
5 parts by weight of the sodium salt of a disproportionated abietic acid,
0.5 parts by weight of the sodium salt of a condensation product of naphthalene sulphonic acid and formaldehyde,
0.5 parts by weight of sodium hydroxide, and
0.5 parts by weight of tetrasodium pyrophosphate.

$y$ was selected as follows:

The value for the quantity of regulator $y$ was varied at follows:

$y_1 = 0.3$ parts by weight,
$y_2 = 0.6$ parts by weight,
$y_3 = 0.65$ parts by weight,
$y_4 = 0.70$ parts by weight,
$y_5 = 0.75$ parts by weight, and
$y_6 = 0.80$ parts by weight.

After the two phases have been mixed, the temperature is increased to 43° C an polymerisation initiated by an activator solution of 2.5 parts by weight of formamidine sulphinic acid in 97.5 parts by weight of pure water. The activator solution is added dropwise.

At the monomer conversion of 65 to 70 %, the residual monomer is removed by steam distillation and the polymer recovered from the latex formed by precipitation with an electrolyte and dried. Table 1 shows Mooney viscosities ML-4'/100° C of the polymers.

Table 1

| $y$ | regulator % by weight | Mooney viscosity (ML-4' at 100°C) |
|---|---|---|
| $y_1$ | 0.3 | 122 |
| $y_2$ | 0.6 | 65 |
| $y_3$ | 0.65 | 52 |
| $y_4$ | 0.70 | 42 |
| $y_5$ | 0.75 | 34 |
| $y_6$ | 0.80 | 30 |

II. Polymerisation example

The following phases are separately prepared and introduced into the reaction vessel:

Monomer phase
100 parts by weight of chloroprene, and
$z$ parts by weight of the xanthogendisulphide of glycerin-1,3-diethyl ether Aqueous phase
120 parts by weight of pure water,
5 parts by weight of the sodium salt of a disproportionated abietic acid,
0.5 parts by weight of the sodium salt of a condensation product of naphthalene sulphonic acid and formaldehyde,
0.5 parts by weight of sodium hydroxide, and
0.5 parts by weight of tetrasodium pyrophosphate.

$z$ was selected as follows:
$z_1 = 0.6$ part by weight, and
$z_2 = 1.0$ part by weight.

After the two phases have been mixed, the temperature is increased to 43° C and polymerisation initiated by an activator solution of 2.5 parts by weight of formamidine sulphinic acid and 97.5 parts by weight of pure water. The activator solution is added dropwise.

At a monomer conversion of 65 to 70 %, the residual monomer is removed by steam distillation, the polymer recovered from the latex formed by precipitation with an electrolyte and dried. Table 2 indicates Mooney viscosities of the products made.

Table 2

| $z$ | regulator % by weight | Mooney viscosity (ML-4' at 100°C) |
|---|---|---|
| $z_1$ | 0.6 | 100 |
| $z_2$ | 1.0 | 37 |

III. Polymerisation example

The following phases are separately prepared and introduced into the reaction vessel:

Monomer phase
100 parts by weight of chloroprene, and
$r$ parts by weight of the xanthogendisulphide of diethylene glycol monoethyl ether.

Aqueous phase
120 parts by weight of pure water,
5 parts by weight of the sodium salt of a disproportionated abietic acid,
0.5 part by weight of the sodium salt of a condensation product of naphthalene sulphonic acid and formaldehyde,
0.5 part by weight of sodium hydroxide, and
0.5 part by weight of tetrasodium pyrophosphate.

$r$ was selected as follows:
$r_1 = 0.3$ part by weight, and
$r_2 = 0.6$ part by weight.

After the two phases have been mixed, the temperature is increased to 43° C and polymerisation initiated by an activator solution of 2.5 parts by weight of formamidine sulphinic acid and 97.5 parts by weight of pure water. The activator solution is added dropwise.

At a monomer conversion of 65 to 70 %, the residual monomer is removed by steam distillation and the polymer recovered from the latex formed by precipitation with an electrolyte and dried. Table 3 indicates Mooney viscosities of the products obtained.

Table 3

| r | regulator % by weight | Mooney viscosity (ML-4' at 100°C) |
|---|---|---|
| r₁ | 0.3 | 137 |
| r₂ | 0.6 | 65 |

IV. Polymerisation example
Aqueous phase
72 parts by weight of pure water,
3 parts by weight of the sodium salt of an alkyl sulphate ($C_{12}H_{25}SO_4Na$),
0.4 part by weight of the sodium salt of the condensation product of naphthalene sulphonic acid and formaldehyde,
1 part by weight of tetrasodium pyrosulphate, and
0.025 parts by weight of sodium hydroxide.
Monomer phase
27 parts by weight of acrylonitrile, and
0.66 part by weight of the xanthogendisulphide of 3-methoxy-1-butanol.

The phases are separately prepared and introduced into a reaction vessel. 63 parts by weight of butadiene are then introduced under pressure.

After mixing, the temperature is adjusted to 20° C and polymerisation activated with 1 % by weight, based on monomers, of potassium persulphate. At a monomer conversion of approximately 75 %, the residual monomer is removed, the latex stabilised and the polymer precipitated from the latex with an electrolyte and subsequently dried.

The polymer has a Mooney viscosity ML-4'/100° C of about 45. If no xanthogendisulphide is present in this polymerisation, Mooney viscosities ML-4'/100° C above 200 are found.

V. Polymerisation example
Preparation of a mixture of a benzene-soluble chloroprene polymer and a benzene-insoluble chloroprene polymer.

1. Preparation of the benzene-insoluble chloroprene polymer

Into a 40-liter autoclave equipped with stirrer, thermometer, inlet pipes and a cooling system are introduced:

14.4 liter of desalted water, 815 g of the sodium salt of a disporportionated abietic acid mixture, 72 g of a condensation product of alkyl naphthalene sulphonic acid and formaldehyde, 36 g of sodium hydroxide and 60 g of tetrasodium pyrophosphate. Then a mixture of 10 620 g of chloroprene, 1380 g of ethylene glycol dimethacrylate and 34 g of n-dodecyl mercaptan is added. The resulting mixture is then heated to 43° C and polymerisation is initiated by adding a catalyst solution of 5 g of formamidine sulphinic acid in 150 g of pure water.

At a conversion of approximately 80 %, polymerisation is stopped by adding a stabiliser solution of:

5 g of phenothiazine and 5 g of p-tert.-butyl pyrocatechol in 500 g of benzene. The resulting polymer latex is then freed from unreacted monomer.

2. Preparation of the benzene-soluble chloroprene polymer

A polymer latex is made in accordance with polymerisation example I using 0.60 parts by weight of the xanthogendisulphide of 3-methoxy-1-butanol.

3. Preparation of a benzene-soluble chloroprene polymer for comparison in the absence of alkoxyxanthogendisulphide is carried out in accordance with polymerisation example I using 0.59 parts by weight of diisopropylxanthogendisulphide.

Admixture of benzene-soluble and benzene-insoluble polychloroprene:

Mixture A:
The polychloroprene latex of Example V 2 is mixed with the polychloroprene latex according to Example V 1 so that the mixture contains 85 parts by weight of the benzene-soluble polychloroprene and 15 parts by weight of the benzene-insoluble polychloroprene. The solid polychloroprene mixture is recovered from the latex mixture by low-temperature coagulation, separation and drying of the solids.

Mixture B:
Mixture B (for comparison) is prepared from the latices of examples V 3 and V 1 in exactly the same way as described in A.

Samples of products A and B are stored at 70° C and the change in their Mooney viscosities over the storage period determined. The results are set out in the following Table:

| Product | Mooney viscosity ML-4' (100°C) after storage for y-days | | | | Increase in Mooney viscosity after 3 days |
|---|---|---|---|---|---|
| | y = 0 | y = 1 | y = 2 | y = 3 | |
| B | 52 | 55 | 60 | 67 | 15 |
| A | 51 | 53 | 54 | 54 | 3 |

Product A (according to the invention) shows practically no change in viscosity and is thus considerably more stable under heat than product B (comparison).

We claim:
1. In the process for aqueous emulsion polymerization of conjugated diolefins, chloroprene or 2,3-dichlorobutadiene in the presence of radical initiators, the improvement comprising carrying out said process in the presence of 0.05 to 30% by weight, based on conjugated diolefin, chloroprene or 2,3-dichlorobutadiene of an alkoxyxanthogendisulphide of the formula

$$R-O-\underset{S}{\overset{\parallel}{C}}-S-S-\underset{S}{\overset{\parallel}{C}}-O-R$$

wherein the R's are equal or different and each represents $R_1O(-CH_2-)_nO(-CH_2-)_{n'}-$ ;

$R_1O - R_2 -$ ;

$\begin{matrix} R_1O-CH_2 \\ \phantom{R_1O-}\diagdown \\ \phantom{R_1O-CH_2}CH- \text{ or} \\ \phantom{R_1O-}\diagup \\ R_1O-CH_2 \end{matrix}$ $R_3O(-(CH_2)_m^-$ wherein $R_1$ is alkyl having 1 to 10 carbon atoms;
$R_2$ is a linear or branched alkylene having 3 to 10 carbon atoms;
$R_3$ is alkyl having 3 to 10 carbon atoms;
$n$ and $n'$ are 2, 3 or 4; and $m$ is 1 or 2.

2. Improved process according to claim 1 wherein said conjugated diolefin has 4 to 8 carbom atoms.

3. The process of claim 1 wherein said conjugated diolefin is butadiene.

4. The process of claim 1 wherein the conjugated diolefin, chloroprene or 2,3-dichlorobutadiene is copolymerized with up to 40% by weight, based on the conjugated diolefin, chloroprene or 2,3-dichlorobutadiene, of an α-olefin.

5. The process of claim 1 wherein the conjugated diolefin, chloroprene or 2,3-dichlorobutadiene is copolymerized with up to 50% by weight of acrylonitrile, styrene or ethyl acrylate.

\* \* \* \* \*